(12) United States Patent
Wang et al.

(10) Patent No.: US 12,196,834 B2
(45) Date of Patent: Jan. 14, 2025

(54) CALIBRATION SYSTEM AND METHOD FOR MAGNETOMETERS

(71) Applicants: COGNITIVE MEDICAL IMAGING LTD., Beijing (CN); INSTITUTE OF BIOPHYSICS, CHINESE ACADEMY OF SCIENCES, Beijing (CN)

(72) Inventors: Fan Wang, Beijing (CN); Yan Zhuo, Beijing (CN); Sijia Yang, Beijing (CN); Shunzi Wu, Beijing (CN)

(73) Assignees: COGNITIVE MEDICAL IMAGING LTD., Beijing (CN); INSTITUTE OF BIOPHYSICS, CHINESE ACADEMY OF SCIENCES, Beijing (CN)

(*) Notice: Subject to any disclaimer, the term of this patent is extended or adjusted under 35 U.S.C. 154(b) by 159 days.

(21) Appl. No.: 18/018,735

(22) PCT Filed: Jul. 30, 2021

(86) PCT No.: PCT/CN2021/109654
§ 371 (c)(1),
(2) Date: Jan. 30, 2023

(87) PCT Pub. No.: WO2022/022690
PCT Pub. Date: Feb. 3, 2022

(65) Prior Publication Data
US 2023/0221394 A1    Jul. 13, 2023

(30) Foreign Application Priority Data

Jul. 30, 2020 (CN) .......................... 202010753611.9

(51) Int. Cl.
*G01V 3/00* (2006.01)
*G01R 33/00* (2006.01)
(Continued)

(52) U.S. Cl.
CPC ....... *G01R 35/005* (2013.01); *G01R 33/0017* (2013.01); *G01R 33/26* (2013.01)

(58) Field of Classification Search
CPC .............. G01R 35/005; G01R 33/0017; G01R 33/0026
(Continued)

(56) References Cited

U.S. PATENT DOCUMENTS 9,791,536 B1    10/2017   Alem et al.
2014/0188422 A1   7/2014   Huber et al.
(Continued)

FOREIGN PATENT DOCUMENTS

CA    2431722 C  *  7/2009   ............. G01C 17/38
CN    1405736 A      3/2003
(Continued)

*Primary Examiner* — Walter L Lindsay, Jr.
*Assistant Examiner* — Frederick Wenderoth
(74) *Attorney, Agent, or Firm* — Scully, Scott, Murphy & Presser, P.C.

(57) ABSTRACT

A calibration system for magnetometers includes magnetometers configured to measure a magnetic field to be measured; a magnetometer holder fixedly mounted on the magnetometer holder; at least one magnetic field generating device having its position fixed relative to the magnetometers, and used to generate a calibration magnetic field distribution in a space to be measured; and a calculation device configured to calculate the magnitudes of magnetic field vectors at the positions of the magnetometers according to the calibration magnetic field distribution generated by the at least one magnetic field generating device in the space to be measured, receive measured magnitudes of the magnetic field vectors from the magnetometers, and calculate detection gain values of the magnetometers on the basis of the calculated magnitudes of the magnetic field vectors and the measured magnitudes of the magnetic field vector.

12 Claims, 9 Drawing Sheets

(51) Int. Cl.
*G01R 33/26* (2006.01)
*G01R 35/00* (2006.01)

(58) Field of Classification Search
USPC .......................................... 324/301
See application file for complete search history.

(56) References Cited

U.S. PATENT DOCUMENTS

2018/0061022 A1* 3/2018 Masumoto ................ G06T 7/97
2018/0313908 A1 11/2018 Knappe et al.

FOREIGN PATENT DOCUMENTS

| CN | 104380040 A | 2/2015 |
| CN | 211178436 U | 8/2020 |
| CN | 112834973 A | 5/2021 |

* cited by examiner

CALIBRATION SYSTEM AND METHOD FOR MAGNETOMETERS

CROSS-REFERENCE TO RELATED APPLICATION

The present application is a U.S. National Phase Entry of PCT International Application No. PCT/CN2021/109654, filed on Jul. 30, 2021, which claims priority of the Chinese Patent Application No. 202010753611.9 filed on Jul. 30, 2020, the disclosure of each of which is incorporated herein by reference in its entirety as part of the present application.

TECHNICAL FIELD

The present invention relates to a calibration system and method for magnetometers, a magnetic detection system and a magnetic detection method. The present invention further relates to a magnetometer holder

BACKGROUND

In the field of weak magnetic detection, it is necessary to calibrate or gauge parameters of the magnetic detectors before working. For example, the magnetic detector of MEG technology with superconducting quantum interference device (SQUID) as the core device needs to have its detector gain value detected and be calibrated periodically (for example, by placing a model that generates known magnetic field intensity).

However, the measurement accuracy of the new optical-pumping atomic magnetometer based on spin-exchange relaxation free effect (SERF) reaches or even exceeds that of the SQUID magnetometer. Also, it can work in an environment not of ultra-low temperature, and without the need for liquid helium cooling. It is small in volume and light in weight, and its low-cost mass production can be realized through semiconductor technology. Because a magnetic field intensity detected by a magnetometer based on SERF effect is calculated through a polarized beam intensity or a polarization angle detected by a photoelectric sensor, in the field of weak magnetic detection based on the atomic magnetometer, in order to obtain accurate detection results, it is necessary to gauge and calibrate the detection gain value of the detector (magnetometer).

Especially for signal detection, tracing and positioning using an array multi-detector magnetometer, accurate calibration of the detector gain value is very important for accurate tracing and positioning. In an existing atomic magnetometer, a coil is used at a position near the air chamber in each detector to generate a magnetic field of a specific intensity during the start-up process of the detector, so as to calibrate the gain of the detector. It is difficult for this method to carry out accurate simultaneous gauging and coordinated calibration of multiple detectors in a working environment with certain changes in the external magnetic field.

Based on this, the present invention provides a calibration system and method for magnetometers, which perform calibration using magnetic field signal sources that can act on all detectors simultaneously, and which carry out coordinated calibration of multiple detectors with said signal sources as the reference signal sources. The calibration system and method can continuously calibrate gain values of the detectors in a recording process, so as to obtain accurate multi-detector magnetic field recording and tracing and positioning results.

SUMMARY

An embodiment of the present invention provides a calibration system for magnetometers, comprising magnetometers configured to measure a magnetic field to be measured; a magnetometer holder, the magnetometers being fixedly mounted on the magnetometer holder, so that spatial positions and orientations of the magnetometers are known; at least one magnetic field generating device for generating a calibration magnetic field distribution in the space to be measured, the position of the at least one magnetic field generating device being fixed relative to the magnetometers; and a calculation device configured to calculate the magnitudes of magnetic field vectors at the positions of the magnetometers according to the calibration magnetic field distribution generated by the at least one magnetic field generating device in the space to be measured, receive magnitudes of the magnetic field vectors measured by the magnetometers from the magnetometers, and calculate detection gain values of the magnetometers based on the calculated magnitudes of the magnetic field vectors and the measured magnitudes of the magnetic field vectors.

An embodiment of the present invention provides a calibration method for magnetometers, comprising: providing magnetometers mounted on a magnetometer holder, the magnetometers being configured to measure a magnitude of a magnetic field at positions of the magnetometers as measured values of the magnetometers; fixing positions of at least one magnetic field generating device relative to the magnetometers, the at least one magnetic field generating device being configured to generate a calibration magnetic field distribution; determining spatial positions and orientations of the magnetometers, and calculating calibration actual values of the magnetic field at the positions of the magnetometers based on the spatial positions and orientations of the magnetometers and the calibration magnetic field distribution; measuring the magnetic field at the positions of the magnetometers to obtain calibration measured values of the magnetic field; calculating detection gain values of the magnetometers based on the calibration measured values and the calibration actual values.

An embodiment of the present invention provides a calibration method for magnetometers, comprising: providing magnetometers mounted on a magnetometer holder, the magnetometers being configured to measure a magnitude of a magnetic field at positions of the magnetometers as measured values of the magnetometers; providing a plurality of magnetic field generating devices, at least one part of the magnetic field generating devices among the plurality of magnetic field generating devices being fixedly disposed on the magnetometers, and the at least one part of the magnetic field generating devices being configured to generate calibration magnetic fields; measuring the calibration magnetic fields by the magnetometers to obtain calibration measured values of the calibration magnetic fields; calculating detection gain values of the magnetometers based on the calibration magnetic fields and the calibration measured values; generating magnetic fields that are fixed or regularly changing with known parameters by another part of the magnetic field generating devices located on the magnetometer holder, the magnetic fields generated being measured by the magnetometers with their gain calibrated to obtain measured values, and calibrating gain values of the magnetometers through the measured values and the changes thereof during a recording process. In this process, the magnetic field generating devices fixed on the magnetometers can be turned off after the initial calibration.

The embodiment of the present invention provides a magnetic detection system, comprising a magnetometer holder; magnetometers, the magnetometers being mounted on the magnetometer holder and measuring magnitudes of magnetic field vectors at their positions as measured values of the magnetometers; magnetic field generating devices, the magnetic field generating devices being disposed at predetermined positions and generating calibration magnetic field distributions; and a calculation device configured to calculate calibration actual values of the magnetic field vectors at the positions of the magnetometers based on the spatial positions and orientations of the magnetometers and the calibration magnetic field distributions, receive calibration measured values of the magnetic field vectors obtained by the magnetometers, and compare the calibration actual values with the calibration measured values to calculate detection gain values of the magnetometers.

An embodiment of the present invention relates to a magnetic detection system, comprising a magnetometer holder; magnetometers, the magnetometers being mounted on the magnetometer holder and measuring the magnitudes of magnetic field vectors at their positions as measured values of the magnetometers; first magnetic field generating devices, the first magnetic field generating devices being disposed at predetermined positions and generating calibration magnetic fields; and a calculation device configured to receive calibration measured values of the calibration magnetic fields obtained by the magnetometers and calculate detection gain values of the magnetometers based on the calibration magnetic fields and the calibration measured values.

An embodiment of the present invention provides a magnetic detection method, comprising: providing magnetometers, the magnetometers being mounted on a magnetometer holder and measuring magnitudes of magnetic field vectors at their positions as measured values of the magnetometers; obtaining detection gain values of the magnetometers using an calibration method as described above; measuring a magnetic field to be measured by the magnetometers; and multiplying measurement results of the magnetometers by the detection gain values to obtain actual values of the magnetic field to be measured.

An embodiment of the present invention provides a magnetometer holder, comprising mounting parts for mounting magnetometers; and at least one magnetic field generating device having the position fixed relative to the magnetometers and being used to generate a calibration magnetic field.

BRIEF DESCRIPTION OF DRAWINGS

In order to explain the technical scheme of the embodiments of the present invention more clearly, the drawings of the embodiments of the present invention will be briefly introduced below. The drawings are only used to show some embodiments of the present invention, but not to limit all embodiments of the invention to them.

DETAILED DESCRIPTION

Figure 1:
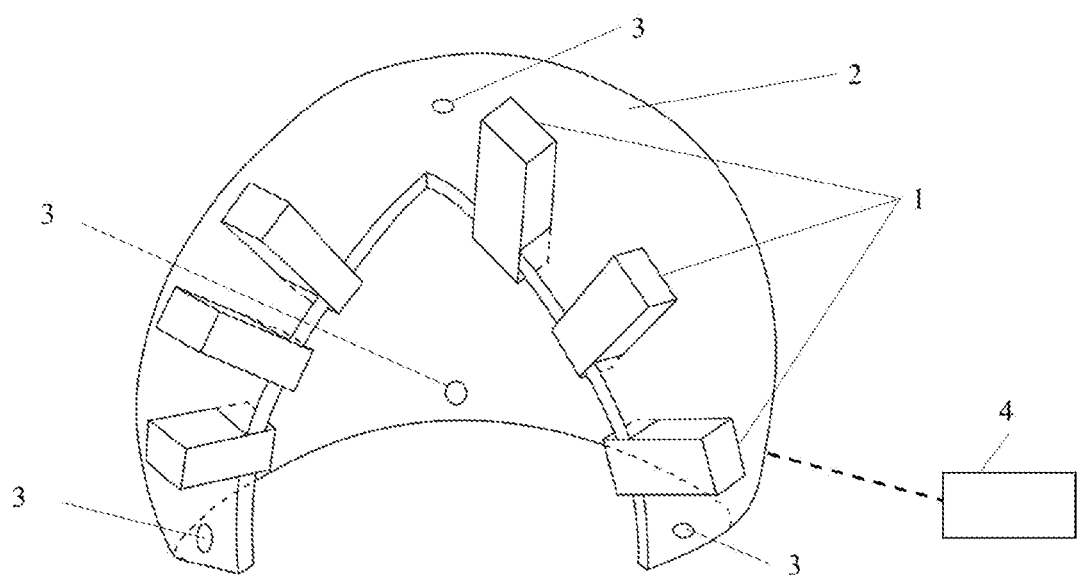
FIG. 1 shows a schematic diagram of a calibration system according to an embodiment of the present invention.

In order to make the purpose, technical scheme and advantages of the technical scheme of the present invention clearer, the technical scheme of the embodiments of the present invention will be clearly and completely described below with reference to the drawings of specific embodiments of the present invention. In the drawings, the same reference numerals represent the same parts. It should be noted that the described embodiments are part of the embodiments of the present invention, but not all of them. Based on the described embodiments of the present invention, all other embodiments obtained by those of ordinary skills in the art without creative labor are within the scope of protection of the present invention.

Unless otherwise defined, the technical terms or scientific terms used here shall have their ordinary meanings as understood by those with ordinary skills in the field to which the present invention belongs. Words "first", "second" and the like used in the specification and claims of the patent application of the present invention do not indicate any order, quantity or importance, but are only used to distinguish different components. Similarly, words "one" or "a" and the like do not necessarily mean quantity limitation. Words "comprising" or "including" and the like mean that the elements or objects appearing before the word encompass the elements or objects listed after the word and their equivalents, without excluding other elements or objects. Words "connected" or "interconnected" and the like are not limited to physical or mechanical connections, but can include electrical connections, whether direct or indirect. "Up", "down", "left", "right" and the like are only used to indicate the relative positional relationship. When the absolute position of the described object changes, the relative positional relationship may also change accordingly.

As the SERF effect-based optical-pumping atomic magnetometer (hereinafter referred to as "magnetometer") conducts magnetic measurement by using the atomic spin effect in a weak magnetic field, and its detection process is related to the influence of the external magnetic field, the gain value of the detector is not only related to the hardware and control parameters of the detector itself, but also affected by a net magnetic field where the detector is located. A magnetic field even in the insensitive direction of the detector, such as along the incident direction of the detection beam, would affect the detection gain of the detector in the sensitive direction. This characteristic is quite different from a traditional SQUID sensitive detector whose gain value is basically stable under different external magnetic fields. The calibration methods used for a traditional SQUID detector array, such as periodically (every power-on test, every warm-up maintenance or every equipment routine maintenance cycle) placing a model with known magnetic field intensity to detect and calibrate the detector gain value, are not suitable for optical-pumping atomic magnetometers.

When conducting signal detection, tracing and positioning with an array multi-detector magnetometer, the positions, directions and gain values of the detectors are very important for accurate tracing and positioning. An existing optical-pumping atomic magnetometer uses a coil to generate a magnetic field with a specific intensity at a position close to the air chamber in each detector during the start-up of the detector, so as to calibrate the gain of the detector. For a single detector, this method is effective and feasible. For a detector array composed of multiple detectors, the magnetic fields generated by the calibration coils will cause crosstalk between the detectors. When one detector is calibrated, the magnetic field generated by it will affect other adjacent detectors. Therefore, for an atomic magnetometer multi-detector array, the existing device cannot conduct calibration simultaneously on all detectors, and the calibration can only be conducted by calibrating each detector in sequence or by calibrating detectors at a certain distance, i.e., calibration at intervals. This not only greatly prolongs the time required for calibration, but also makes it impossible to calibrate all detectors accurately when the external magnetic field changes. In a working environment with a certain change in the external magnetic field, the multi-detector system composed of existing detectors cannot carry out continuous calibration or continuous calibration with a certain interval, and it is difficult to conduct accurate multi-detector simultaneous recording and signal tracing and positioning. The present invention uses a calibration system and method based on external magnetic field signal sources to perform coordinated calibration of the multiple detectors, and the signal sources can be used as reference signal sources to continuously calibrate gain values of the detectors during the recording process, so as to obtain accurate multi-detector magnetic field recording results.

It should be noted that the terms "optical-pumping atomic magnetometer", "atomic magnetometer" and "magnetometer" mentioned in the present disclosure refer to an optical-pumping atomic magnetometer based on spin-exchange relaxation free effect (SERF). The present disclosure is not limited to this, and calibration systems and calibration methods applicable to other magnetic detectors that can be obtained by those skilled in the art through modifications and variations according to the present disclosure are also within the scope of protection of the present disclosure.

Embodiments of the present disclosure will be described below with reference to the accompanying drawings.

Figure 2:
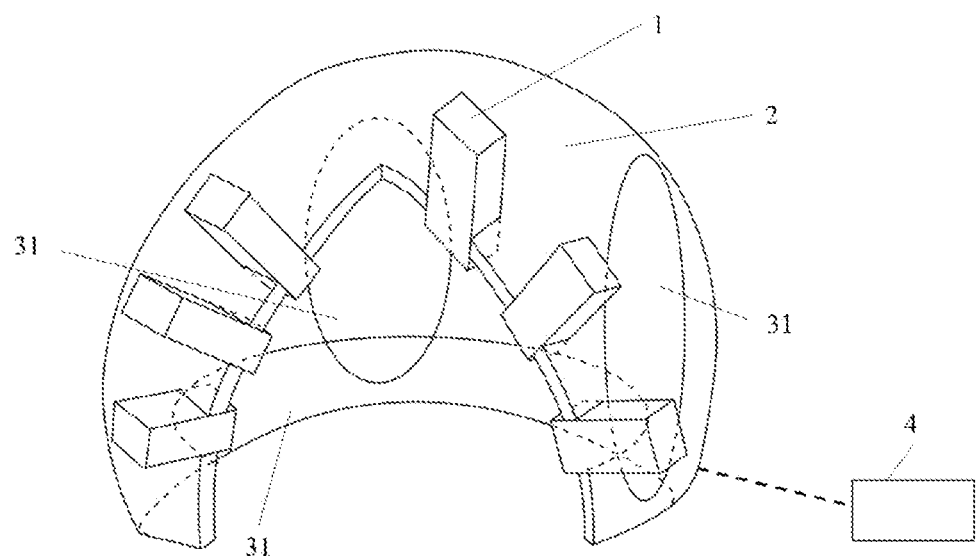
FIG. 2 shows a schematic diagram of a calibration system according to another embodiment of the present invention.
Figure 3:
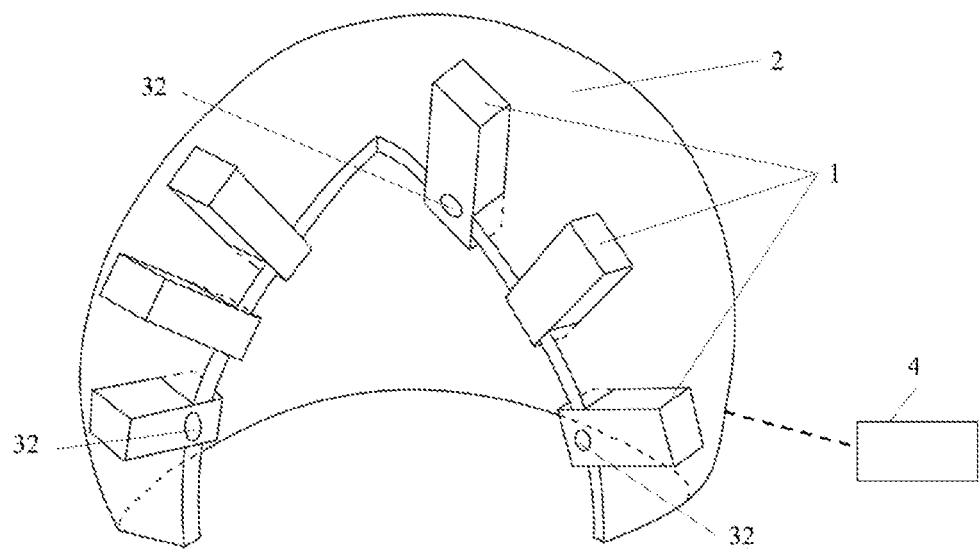
FIG. 3 shows a schematic diagram of a calibration system according to yet another embodiment of the present invention.
Figure 4:
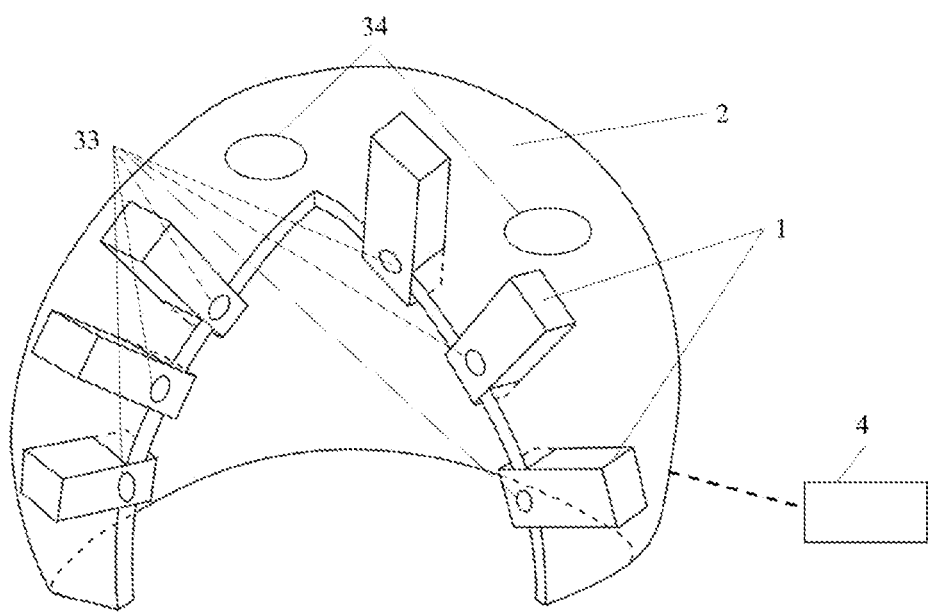
FIG. 4 shows a schematic diagram of a calibration system according to a variant embodiment of the present invention.

FIG. 1 shows a schematic diagram of a calibration system according to an embodiment of the present invention. FIG. 2 shows a schematic diagram of a calibration system according to another embodiment of the present invention. FIG. 3 shows a schematic diagram of a calibration system according to yet another embodiment of the present invention. FIG. 4 shows a schematic diagram of a calibration system according to a variant embodiment of the present invention.

An embodiment of the present invention provides a calibration system for magnetometers, comprising: magnetometers configured to measure a magnetic field to be measured; a magnetometer holder, the magnetometers being mounted on the magnetometer holder; at least one magnetic field generating device having the position fixed relative to the magnetometers and being used to generate a calibration magnetic field; and a calculation device used for obtaining measurement results of the magnetometers. The magnetometers are configured to measure the calibration magnetic field generated by the at least one magnetic field generating device, and the calculation device calculates detection gain values of the magnetometers based on the measurement results by the magnetometers.

By way of example, the at least one magnetic field generating device may be disposed on at least one of the magnetometer holder, the space to be measured, or the magnetometers. In actual use, selection can be made according to requirements. No matter where the magnetic field generating devices are located, the relative spatial positions and orientations of the magnetic field generating devices and all magnetometers are fixed and known, or can be gauged continuously so as to be known. In addition, the calibration magnetic fields generated by the magnetic field generating devices are known, so the magnetic field distributions of the calibration magnetic fields at positions where the magnetometers are located are known, and the detection gain values of the magnetometers can be calculated based on measurement results by the magnetometer and the magnetic field distributions.

Compared with the case in which each magnetometer uses its own signal source for calibration, the calibration system of the present invention has the advantage that it will not cause crosstalk with the existing magnetometers during calibration, thus not affecting the work of other detectors. In addition, it is possible to perform gauging quickly and simultaneously, and it is even possible to perform continuous gauging and continuous calibration while the magnetometers are recording signals.

At the same time, because continuous calibration can be performed and the detection gain values can be continuously gauged, the calibration system of the present invention can expand the dynamic range of detection of the magnetometers to the nonlinear range of the detectors without sacrificing the sensitivity, thus expanding the detection range.

The calibration system includes magnetometers 1, a magnetometer holder 2, at least one magnetic field generating device 3 and a calculation device 4. The magnetic field generating devices 3 may be configured to generate known or preset calibration magnetic field distributions, which refer to magnetic field distributions that can be calculated according to the input of the magnetic field generating devices 3 or other parameters or can be obtained by other means, and the magnetic field distributions are used to calibrate the detection gain values of the magnetometers 1. Through the magnetic field distributions, the magnitudes of magnetic field vectors at certain spatial positions and orientations in the magnetic field distributions can be obtained. The magnetometers 1 are configured to measure a magnetic field to be measured in a space to be measured, such as a brain magnetic signal of a subject. In addition, the magnetometers 1 can also be used to obtain information about biological magnetic fields of other parts, depending on the positions where the magnetometers 1 are set. As shown in FIG. 1, for example, a magnetometer holder 2 is in the form of a helmet, which can be fixedly disposed relative to a space to be measured (e.g., the head of a subject), and includes at least one mounting part (not shown) with a predetermined orientation, allowing the magnetometers 1 to each be disposed on the mounting part in a specific direction at a first depth. Preferably, the magnetometer holder 2 comprises a plurality of mounting parts, and the magnetometers 1 are respectively mounted on each mounting part and fixed relative to the magnetometer holder. Therefore, by knowing information of each mounting part, for example, when the mounting part is a mounting hole, by knowing the spatial direction of the axial direction of the mounting hole and the depth of a magnetometer 1 inserted into the mounting hole, the spatial position and orientation information of the magnetometer 1 can be determined.

Therefore, a magnetometer 1 is fixedly mounted on a magnetometer holder 2, so once the mounting is completed, the relative position and orientation between the magnetometer 1 and the mounting hole can be fixed and determined.

In one embodiment, the mounting parts may include, for example, a detection electrode, through which it can be detected that a mounting hole has been mounted with a magnetometer, as well as the mounting depth of the magnetometer. In another embodiment, the mounting parts may be provided with a sensor to sense mounting information of the magnetometer (e.g., the mounting depth of the magnetometer), and to sense the identification code of the magnetometer, and also to send the mounting information of the magnetometer, such as the mounting depth of the magnetometer, the identification code of the magnetometer, and specific information of the mounting part on which the magnetometer is mounted (e.g., the spatial orientation of the mounting part) to the calculation device, so that the calculation device can obtain the spatial position and orientation information of the magnetometers.

It should be noted that the detectors of the magnetometers 1 are vector detectors, and the detected magnetic field information is vector information, which is different from the traditional EEG detection that only detects scalar signals of the electrodes. Therefore, the magnetic field vector information detected by the detectors needs to be measured. Also, the detector of a magnetometer 1 may be arranged to detect the magnetic field intensity along the longitudinal axis direction (length direction) of the magnetometer 1.

The "space to be measured" described in the present disclosure includes, but is not limited to, the head, abdomen or other body parts of a subject, and other objects the magnetic field intensity of which can be detected. Those skilled in the art can make adaptive selections according to the actual measurement applications, and the present disclosure does not pose limitation on this.

As shown in FIG. 1, the calibration system includes a plurality of magnetic field generating devices 3, which are respectively arranged at different spatial positions fixed relative to the magnetometers 1.

Optionally, the plurality of magnetic field generating devices 3 can be arranged on at least one of the magnetometer holder 2, the space to be measured or the magnetometers 1.

In the embodiment shown in FIG. 1, the calibration system includes four magnetic field generating devices 3, which are respectively arranged at four different spatial positions on the magnetometer holder 2. For example, three of the magnetic field generating devices 3 are located at the third parts of the lower end circumference of the magnetometer holder 2 shown in FIG. 1, and the other magnetic field generating device 3 is located at the top right upper position of the magnetometer holder 2. The present disclosure is not limited to this. The magnetic field generating devices 3 can also be disposed at other spatial positions on the magnetometer holder 2, as long as their positions and orientations relative to the magnetometers are fixed. The number of magnetic field generating devices 3 can also be increased or decreased according to actual requirements.

The calculation device 4 is connected with the magnetometers 1 and the magnetic field generating devices 3 through wired or wireless communication (shown by dotted lines in the figure). Common calculation devices in the field, including but not limited to a CPU, a DSP, a computer, a workstation, etc., can be adopted for calculation device 4.

Figure 5:
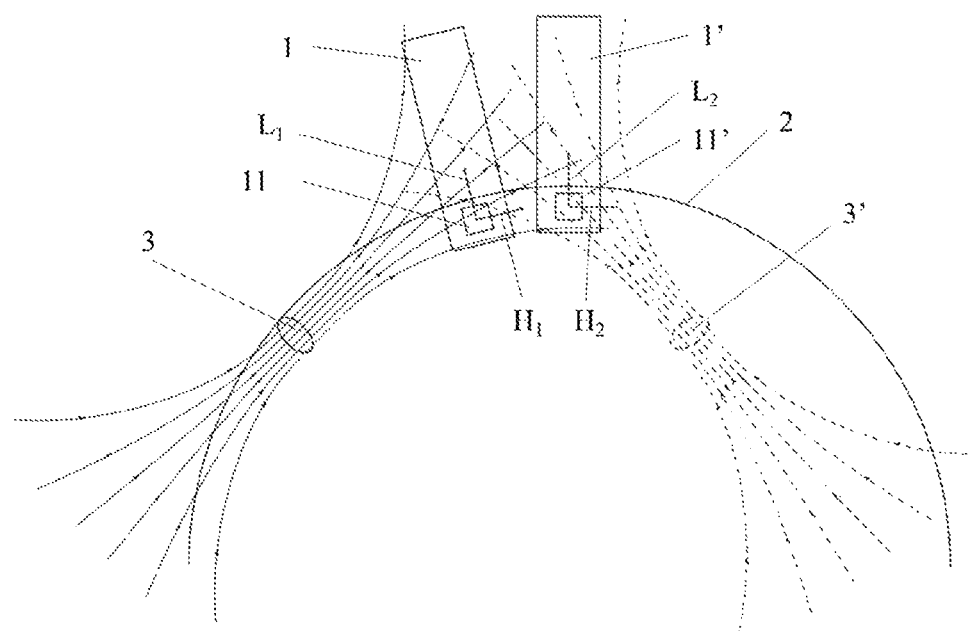
FIG. 5 shows a schematic diagram of spatial distributions of calibration magnetic fields generated by magnetic field generating devices according to an embodiment of the present invention.

By way of example, the magnetic field generating devices 3 may be coil loops or dipoles immersed in a conductive solution. For example, in this embodiment, the magnetic field generating devices 3 are coil loops composed of exciting coils, which can generate spatial magnetic fields when energized, as shown in FIG. 5. Therefore, the magnetic field distributions of the magnetic field generating devices 3 in space can be calculated according to the current of the coil loops, the size of the coil loops, the number of the coil turns and other parameters, thereby the magnitude and direction of the magnetic field vector at a specific position in the space can be calculated. Optionally, the magnetic field generating devices 3 can also be dipoles immersed in a conductive solution.

By way of example, the calibration system may further include a gauging device for gauging the calibration magnetic fields generated by the magnetic field generating devices. The gauging device may be disposed on or near the magnetic field generating devices 3 to realize continuous gauging, or it may be separately arranged and conducts gauging for the magnetic field generating devices 3 every time a magnetic field generating device 3 needs to be gauged.

By way of example, the frequency ranges of the calibration magnetic fields generated by the magnetic field generating devices 3 are set to be outside the frequency range of the magnetic field to be measured. For example, the frequency ranges of the calibration magnetic fields generated by the magnetic field generating devices 3 are higher than the frequency range of the magnetic field to be measured, so that crosstalk in the detection results can be prevented. For example, the frequency range of the magnetic field to be measured (such as brain magnetic signal) is 1-80 Hz. Optionally, the frequency ranges of the calibration magnetic field distributions generated by the magnetic field generating devices 3 are in the range of 80 Hz to 200 Hz. Optionally, the frequency ranges of the calibration magnetic fields generated by the magnetic field generating devices 3 may be greater than 80 Hz, such as 80-100 Hz, 80-120 Hz, 100-200 Hz or greater than 200 Hz. In addition, the frequency ranges of the calibration magnetic fields generated by the magnetic field generating devices 3 may be smaller than the frequency range of the magnetic field to be measured, for example, less than 40 Hz. By way of example, the frequency of the calibration magnetic field distribution generated by each of the plurality of magnetic field generating devices 3 is different, so different magnetic field generating devices 3 can be distinguished in the frequency domain.

By way of example, the calibration system also includes a time domain-frequency domain converter (not shown), which is configured to convert time domain signals measured by the magnetometers into frequency domain signals by Fourier transform or other algorithms, and calculate measured values of target corresponding to the magnetometers through the calibration measured values that correspond to the frequencies of the calibration magnetic fields.

Figure 6:
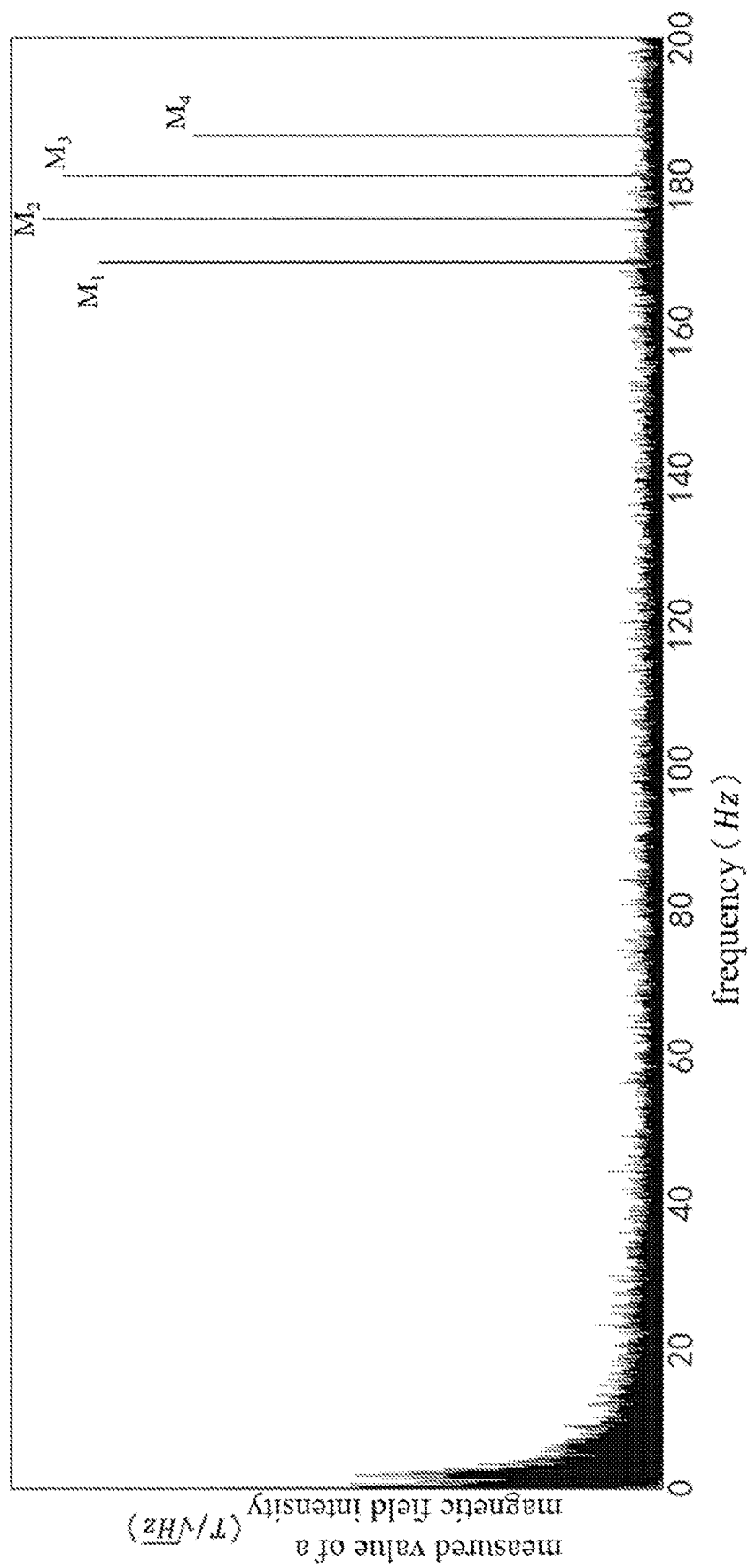
FIG. 6 shows a diagram of distributions of measured values of magnetic field intensities obtained by the calculation device of the embodiment shown in FIG. 1 in the frequency domain.

The time domain signals from the magnetometers, converted by the converter, become frequency domain signals as shown in FIG. 6, for example, and signals with different frequencies each have a peak value in the frequency domain. The time domain-frequency domain converter can be an independent conversion chip or an algorithm built into the calculation device.

FIG. 6 is a diagram showing the distribution of the measured value of a magnetic field intensity, obtained by a calculation device of the embodiment shown in FIG. 1, in the frequency domain. The result in FIG. 6 is the measured value of the magnetic field intensity calculated by the calculation device for one of the magnetometers 1.

The four magnetic field generating devices 3 are excited at different frequencies, so that the calibration magnetic field generated by each magnetic field generating device 3 has a different frequency, such as 173 Hz, 178 Hz, 183 Hz and 188 Hz. The magnetic field intensity generated by the four magnetic field generating devices 3 has four peaks in frequency domain, and the measured values of them are M1, M2, M3 and M4, respectively, as shown in FIG. 6. Different magnetic field generating devices 3 can be distinguished and marked in the frequency domain space through the different calibration magnetic field frequencies, and there will be no interference or crosstalk between them, which is convenient for measurement and calibration operation. FIG. 2 shows a schematic diagram of a calibration system according to another embodiment of the present disclosure. Different from the embodiment shown in FIG. 1, this embodiment adopts larger-sized magnetic field generating devices 31, which can form calibration magnetic fields with more uniform distributions in space, thus facilitating a convenient calibration.

FIG. 3 shows a schematic diagram of a calibration system according to yet another embodiment of the present disclosure. Different from the previous embodiment, the magnetic field generating devices 32 of this embodiment are fixedly arranged on at least one of the plurality of magnetometers, such as on three magnetometers, as shown in FIG. 3.

In some embodiments, the magnetic field generating devices can also have other arrangements according to calibration requirements. For example, a first magnetic field generating device 33 can be fixedly disposed on each magnetometer 1, and at least one second magnetic field generating device 34, such as two second magnetic field generating devices 34, can further be fixedly disposed on the magnetometer holder 2, as shown in FIG. 4.

A calibration method according to an embodiment of the present disclosure will be described below with reference to the drawings.

Figure 7:
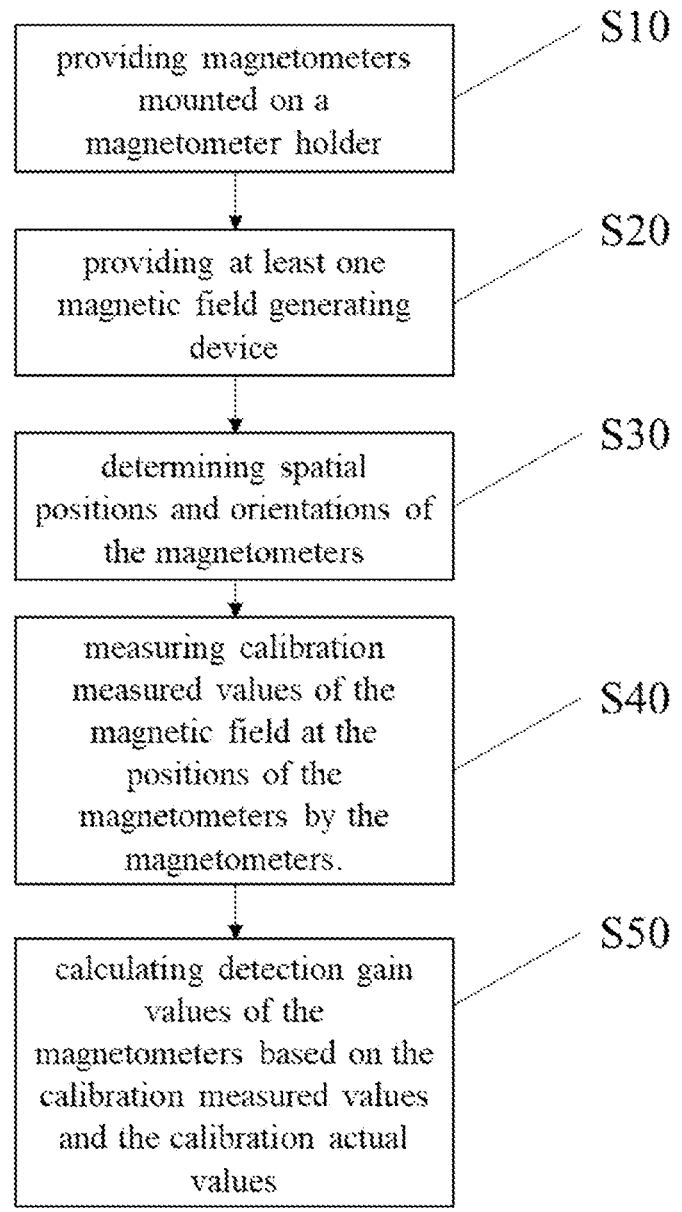
FIG. 7 shows a flowchart of a calibration method for magnetometers according to an embodiment of the present invention.

FIG. 5 shows a schematic diagram of the spatial distributions of the calibration magnetic fields generated by the magnetic field generating devices according to an embodiment of the present invention. FIG. 7 shows a flowchart of a calibration method for magnetometers according to an embodiment of the present invention.

As shown in FIG. 7, the calibration method includes the following steps:

S10. providing magnetometers mounted on a magnetometer holder, the magnetometers being configured to measure magnitudes of a magnetic field at positions of the magnetometers as measured values of the magnetometers.

S20. providing at least one magnetic field generating device, the at least one magnetic field generating device having the position fixed relative to the magnetometers, and the at least one magnetic field generating device generating a known or predetermined spatial magnetic field distribution.

S30. determining spatial positions and orientations of the magnetometers, and based on the spatial positions and orientations of the magnetometers and the calibration magnetic field distribution, calculating calibration actual values of the magnetic field at the positions of the magnetometers.

S40. measuring calibration measured values of the magnetic field at the positions of the magnetometers by the magnetometers.

S50. calculating detection gain values of the magnetometers based on the calibration measured values and the calibration actual values.

In step S10, the arrangement of the magnetometers 1 and the magnetometer holder 2 in the embodiment shown in FIGS. 1-3, for example, can be adopted, which will not be described in detail here.

In step S20, the magnetic field generating devices of the previous embodiment can be adopted for the magnetic field generating devices 3. During the calibration operation, the magnetic field generating devices 3 are turned on to generate calibration magnetic fields, which will form spatial magnetic field distributions, as shown in FIG. 5. In an embodiment where the magnetic field generating devices 3 are coils, the parameters of the calibration magnetic field distributions can be obtained by pre-gauging, and the spatial magnetic field distributions of the calibration magnetic fields can be obtained through computational simulation of Maxwell's equations and Jefimenko's equations which are based on Maxwell's equations. In an actual calculation, the equations under an approximate condition of quasi-static limit, Biot-Savart Law, can usually be used for calculation:

$$\vec{B} = \frac{\mu_0}{4\pi} \int_L \frac{Idl \times \vec{e_r}}{r^2}$$

wherein $\mu_0$ is permeability of vacuum, I is the source current, L is the integral path, dl is the infinitesimal line element of the source current r,$\vec{e_r}$ is the unit vector of the current element pointing to the field point to be analyzed. This simulation step can also be implemented in the calculation device 4. Based on the spatial magnetic field distributions, the magnitude of a magnetic field vector at any point in space can be calculated.

Therefore, in step S30, as long as the position of any magnetometer 1 in space is known, the magnitude of an actual value $M_0$ of a calibration magnetic field at the position of this magnetometer 1 can be obtained. The spatial positions of the magnetometers 1 can be determined by various methods, which will be further described below.

In step S40, the magnetometer 1 measures the magnitude of magnetic field of a calibration magnetic field at the position of the magnetometer 1, and obtains a measured value of calibration $M_A$.

In step S50, the detection gain value is calculated by the calculation device 4 based on the measured value of calibration $M_A$ and the calculated actual value of calibration $M_0$. This detection gain value can be used to calibrate the difference between the measured value of the magnetometer 1 and the actual value.

By way of example, the detection gain value may comprise a detection gain value K of the magnetometer. The detection gain value K is obtained by dividing the actual value $M_0$ of the calibration magnetic field by the measured value of calibration $M_A$, namely:

$$K = \frac{M_0}{M_A}$$

Based on the detection gain value K, the magnetometer 1 can be calibrated. For example, when the magnetometer 1 is actually working, the signal value of the magnitude of the actual magnetic field can be obtained by multiplying the signal of the magnitude of the magnetic field measured by the magnetometer 1, i.e., the measured value of target, by the detection gain value K. In practice, the gain response of a detector at different frequencies may be nonlinear, and the gain values for different frequencies can be calculated by pre-calibrated detection gain values.

FIG. 5 is taken as an example to describe a calibration method of the present disclosure. The embodiment shown in FIG. 5 is only an example, and those skilled in the art can make changes and modifications based on the principle of FIG. 5, the variations and modifications being still within the scope of protection of the present disclosure.

For example, FIG. 5 shows two magnetometers, a first magnetometer 1 and a second magnetometer 1'. The first magnetometer 1 includes a detector 11 accommodated therein, and the second magnetometer 1' includes a detector 11' accommodated therein. The detectors 11 and 11' are the components of the magnetometers that actually detect the magnitude of the magnetic field, so positions of the detectors 11 and 11' can be used as positions of the magnetometers for calibration, and the preset magnetic field distribution can also be calculated based on the positions of the detectors 11 and 11'.

In this example, two magnetic field generating devices are shown, namely the first magnetic field generating device 3 and the second magnetic field generating device 3'. In this example, positions of the two magnetic field generating devices are not limited, and one can refer to the arrangement pattern in the previous embodiment. The first magnetic field generating device 3 and the second magnetic field generating device 3' respectively generate calibration magnetic fields, the distributions of which are shown by the magnetic lines of force in FIG. 5.

The distributions of the calibration magnetic fields of the first magnetic field generating device 3 and the second magnetic field generating device 3' can be calculated. For example, at the detector 11 of the first magnetometer 1, the magnetic field formed by superimposing the calibration magnetic fields generated by the first magnetic field generating device 3 and the second magnetic field generating device 3' can be decomposed into a magnetic field component $L_1$ along the longitudinal direction of the first magnetic field generating device 3 and a magnetic field component $H_1$ in the transverse direction. Similarly, at the detector 11' of the second magnetometer 1', the magnetic field formed by superimposing the calibration magnetic fields generated by the first magnetic field generating device 3 and the second magnetic field generating device 3' can be decomposed into a magnetic field component $L_2$ along the longitudinal direction of the second magnetic field generating device 3' and a magnetic field component $H_2$ in the transverse direction.

Usually, the detector of a magnetometer measures the magnetic field component along the longitudinal direction. The present disclosure is not limited to this, and the magnetometer can also be changed in its configuration to measure the magnetic field component in the transverse direction or the overall magnetic field vector.

In this example, the detectors of the magnetometers measure the magnetic field components along the longitudinal directions, that is, corresponding to $L_1$ and $L_2$, respectively. Furthermore, the first magnetic field generating device 3 and the second magnetic field generating device 3' are operated to generate a predetermined magnetic field distribution, and the magnetometers 1 and 1' are used respectively to measure the magnitude of the magnetic field and obtain measured values $M_1$ and $M_2$. By substituting the above results into the aforementioned equations, the detection gain values of the magnetometer 1 and the magnetometer 1', namely the detection gain values $K_1$ and $K_2$, can be obtained respectively as follows:

$$K_1 = \frac{L_1}{M_1}$$

$$K_2 = \frac{L_2}{M_2}$$

When the deviation of the gain values calculated with the calibration signals from different magnetic field generating devices is less than a certain range ΔK, the multiple gain values are averaged or squared averaged to increase the calibration accuracy. When one or more gain values are significantly deviated from others, it is suggested that the magnetic field generating devices, the detectors or the detector holder may be abnormal, which should be inspected and repaired.

By way of example, the calibration method may further include gauging the calibration magnetic fields generated by the magnetic field generating devices using a gauging device.

By way of example, the calibration method may further include determining whether the deviation of the gain values of at least one magnetometer among a plurality of magnetometers for different magnetic field generating devices is greater than a threshold value, and when the detection gain value of the at least one magnetometer is greater than a threshold value, replacing the at least one magnetometer or inspecting the magnetic field generating devices.

For example, when a certain deviation of the gain values of most magnetometers exceeds a threshold, inspect the magnetic field generating devices or replace at least one magnetic field generating device. The threshold can be set in advance, for example, the threshold is set in the range of ±1%. If deviation between gain values calculated by all or most of the magnetometers for a certain magnetic field generating device and gain values calculated for other magnetic field generating devices is greater than the threshold, it means that this magnetic field generating device may have failed or moved in position. If deviation of detection gain values of a certain magnetometer for different magnetic field signal sources is greater than the threshold, it means that this magnetometer may have failed or moved in position, and at this time it is necessary to replace this magnetometer or readjust its position.

By way of example, the threshold may be between 0.1% and 5%, which is set according to the detectors, the supporting device and different characteristics of the application. It can be understood by those skilled in the art that the threshold value can be 0.1 to 5% or −5% to −0.1%. That is, the threshold represents the maximum value of the degree of deviation, so it can be either positive or negative.

Figure 8:
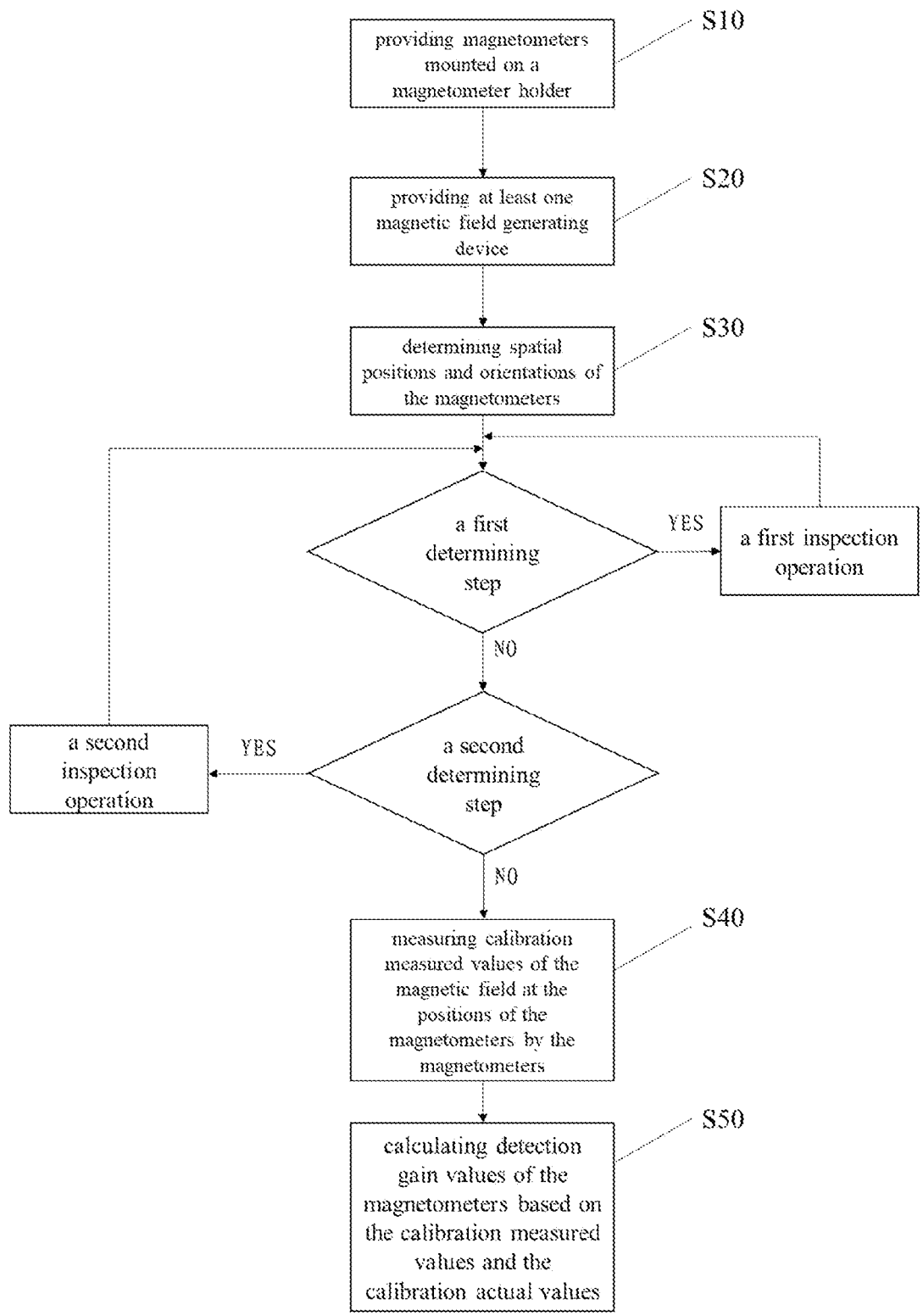
FIG. 8 shows a flowchart of a calibration method for magnetometers according to another embodiment of the present invention.

FIG. 8 shows a flowchart of a calibration method for magnetometers according to another embodiment of the present invention. Different from the embodiment shown in FIG. 7, this embodiment comprises a plurality of magnetic field generating devices, and comprises the above-mentioned determining and inspection steps.

After step S30, first, a first determining step is performed to determine whether deviation of detection gain values of at least one part of the magnetometers for the frequency of one same calibration magnetic field distribution from those for the frequencies of other calibration magnetic field distributions is greater than a threshold value. For example, the at least one part of the magnetometers are at least 80% of the magnetometers, or all of the magnetometers.

If the deviation is greater than the threshold, a first inspection operation is performed, such as gauging the magnetic field generating device that generates the calibration magnetic field distribution or replacing the magnetic field generating device. After the first inspection operation, the first determining step is repeated until the deviation of the detection gain values of most magnetometers for the frequency of the calibration magnetic field distribution is less than or equal to the threshold.

If the first determining step is passed, that is, the above-mentioned deviation is less than or equal to the threshold, one can move on to the second determining step to determine whether the deviation of the detection gain values of a magnetometer for different magnetic field generating devices is greater than the threshold.

If the deviation is greater than the threshold, the second inspection operation is performed, such as replacing the magnetometer, and the first determining step is repeated until the deviation of the detection gain values for different magnetic field generating devices is less than or equal to the threshold.

By way of example, the threshold in the above two determining steps is in the range of 0.1-5%. For example, the value of the threshold is 0.1%, 0.5%, 1%, 2% or 5%. When the deviation in the above two judgment steps is greater than the threshold, an inspection operation is performed.

In this embodiment, by introducing two determining and inspecting steps, the normal operation of the magnetic field generating devices and the accuracy of the detection gain values of the magnetometers can be ensured, and the reliability of the system and the accuracy of the measurement results can be improved.

By way of example, determining the spatial positions and orientations of the magnetometers comprises determining the spatial positions and orientations of the magnetometers through the mounting positions and orientations of the magnetometers on the magnetometer holder or through photographing positioning markers disposed on the magnetometers by a photogrammetry system.

In another embodiment not shown, a method for continuously calibrating the magnetometers is also provided, which is especially suitable for a case where the magnetometer holder is flexible (e.g., a flexible helmet), but the present invention is not limited to this, and can also be applied to an example of a rigid holder. Sometimes the person wearing the helmet cannot avoid head movement, so that the orientations and positions of the magnetometers will change to some extent. In this case, by adopting a magnetometer calibration system according to the present disclosure, the magnetometers can be calibrated at the same time when they are conducting the measurement or at intervals and separated from the measurement. Since the frequencies of the magnetic fields generated by the magnetic field generating devices are different from the frequency of the magnetic field to be measured by the magnetometers, even if the magnetometers are calibrated at the same time of measurement, it is possible, through the difference in frequencies, to extract signals with predetermined frequencies from the measurement results of the magnetometers as measured values. For example, the time domain signals measured by the magnetometers are converted into frequency domain signals by Fourier transform or other algorithms with a time domain-frequency domain converter, and the measured values of target corresponding to the detector magnetometers are calculated through the calibration measured values corresponding to the frequencies of the calibration magnetic fields.

Meanwhile, the positions and orientations of the magnetometers can be measured in real time by using a dynamic measurement system (see the applicant's prior application CN201911190087.2, which is incorporated herein by reference in its entirety). The position and orientation information of the magnetometers measured by the dynamic measurement system is input into the calculation device, so that the calculation device, based on the position and orientation information and the parameters of the magnetic field generating devices, calculates the magnitudes of the magnetic field vectors of the magnetic field distributions generated by the magnetic field generating devices at the positions where the magnetometers are located as calibration actual values of the magnetic field, and compares the calibration measured values with the calculated calibration actual values, so as to dynamically calibrate the magnetometers, that is, dynamically adjust the gains of the magnetometers. By dynamically adjusting the gain values of the magnetometers and applying the adjusted gain values to the measured values of target by the magnetometers, more accurate measurement can be realized.

Figure 9:
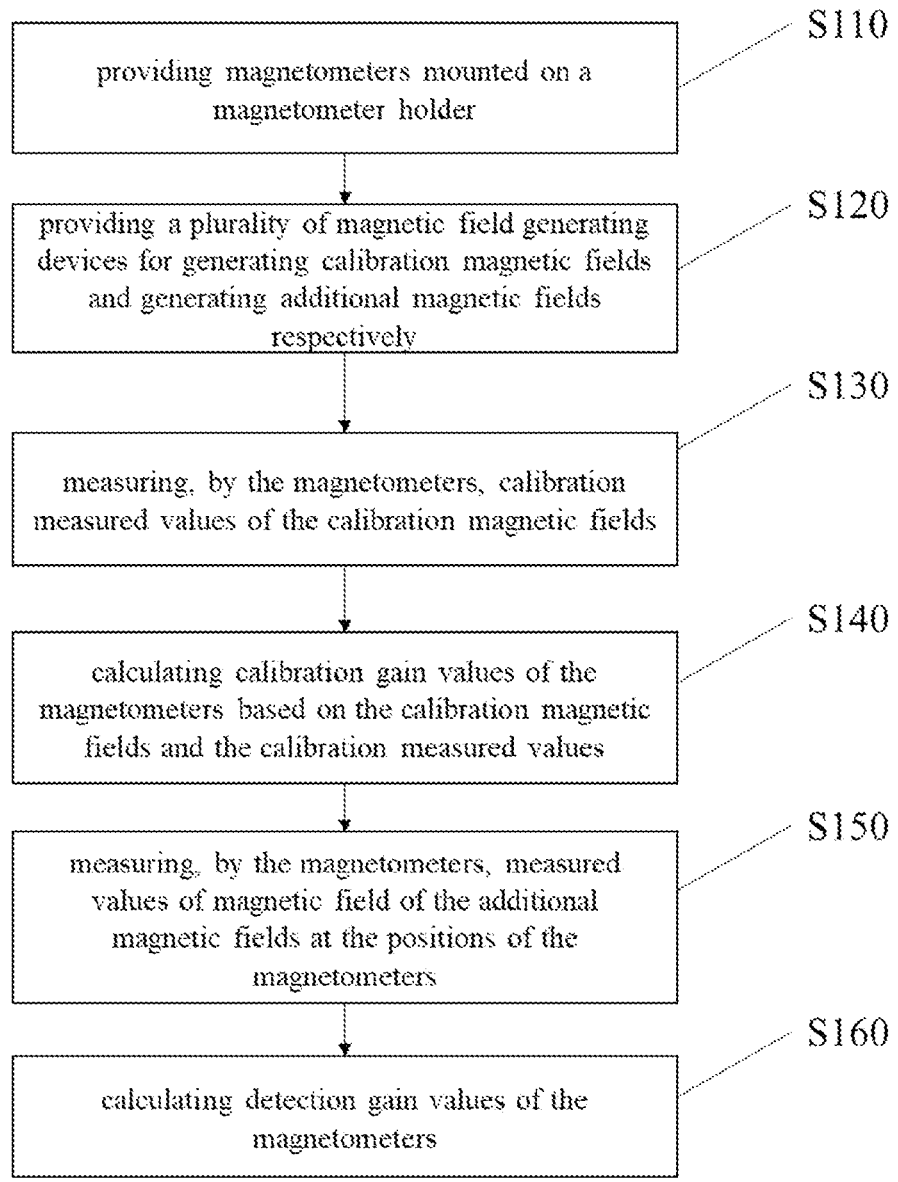
FIG. 9 shows a flowchart of a calibration method for magnetometers according to yet another embodiment of the present invention.

FIG. 9 shows a flowchart of a calibration method for magnetometers according to yet another embodiment of the present invention. For convenience of description, the following will mainly focus on the differences between this embodiment and the previous embodiments, and similar or identical steps and features will be omitted or briefly described.

As shown in FIG. 9, the calibration method comprises the following steps:

S110. providing magnetometers 1 mounted on a magnetometer holder 2, the magnetometers 1 being configured to measure the magnitude of a magnetic field at positions of the magnetometers 1 as measured values of the magnetometers 1.

S120. providing a plurality of magnetic field generating devices, at least one part of the magnetic field generating devices 33 among the plurality of magnetic field generating devices being fixedly disposed on the magnetometers 1, and at least another part of the magnetic field generating devices 34 among the plurality of magnetic field generating devices having the position fixed relative to the magnetometers 1, and the at least one part of the magnetic field generating devices 33 generating calibration magnetic fields, and the another part of the magnetic field generating devices 34 generating additional magnetic fields which are fixed or vary with known parameters.

S130. measuring, by the magnetometers 1, the calibration magnetic fields and obtaining calibration measured values $M_A$ of the calibration magnetic fields.

S140. calculating calibration gain values K of magnetometers 1 based on the calibration magnetic fields and the calibration measured values.

S150. measuring, by the magnetometers 1, the additional magnetic fields at positions of the magnetometers 1 and obtaining measured values of magnetic field $M_B$ of the additional magnetic fields.

S160. during a working process of the magnetometers 1, measuring the additional magnetic fields at the positions of the magnetometers 1 and obtaining measured working values of magnetic field $M_C$ of the additional magnetic fields, and calculating detection gain values K' of the magnetometers 1 based on the measured values of magnetic field $M_B$, the parameters of the additional magnetic fields and the measured working values of magnetic field $M_C$. During this process, the magnetic field generating devices 33 fixed on the magnetometers can be turned off.

Different from the previous embodiments, this embodiment uses magnetic field generating devices 33 fixedly disposed on the magnetometers to generate the calibration magnetic fields, and the calibration magnetic fields are known. Therefore, there is no need to determine the spatial positions and orientations of the magnetometers, and there is no need to calculate the calibration actual values of the magnetic fields at the positions of the magnetometers based on the spatial positions and orientations of the magnetometers and the calibration magnetic field distributions, thus omitting the steps of determining the spatial positions and orientations of the magnetometers and calculating the spatial magnetic field distributions.

The magnetometers 1 and the magnetometer holder 2 in step S110 can be arranged as in the embodiment shown in FIG. 4, for example, and will not be described in detail here.

In step S120, the magnetic field generating devices in the previous embodiment can be adopted as the magnetic field generating devices 33. During the calibration operation, the magnetic field generating devices 33 are turned on to generate calibration magnetic fields. Since the magnetic field generating devices 33 are fixedly disposed on the magnetometers 1, the magnetic fields generated by the magnetic field generating devices 33 at the magnetometers 1 can be considered known. In step S130, the calibration measured values $M_A$ of the calibration magnetic fields are measured by the magnetometers 1. The actual values of magnetic field generated by the calibration magnetic fields are given to be $M_0$.

In step S140, the calibration gain values K are calculated by the calculation device 4 based on the calibration measured values $M_A$ and the actual values of magnetic field $M_0$. The method of calculating the calibration gain values K and the method of measuring the actual signal values of the magnitudes of the magnetic fields based on the calibration gain values K have been described in the previous embodiment (in the previous embodiment as the detection gain values K), which will not be repeated here.

In addition, each magnetometer 1 may be provided with a magnetic field generating device 33, and in step S140, the calibration gain value K of each magnetometer 1 may be measured and it may be recorded in the calculation device 4.

Optionally, the magnetic field generating devices 34 may be disposed on the magnetometer holder 2 or the space to be measured. For example, as shown in FIG. 4, two magnetic field generating devices 34 are fixedly disposed at different positions of the magnetometer holder 2, and the magnetic field generating devices 34 may have the same configuration as the magnetic field generating devices 33. Optionally, the number and positions of the magnetic field generating devices 34 can be selected as required, and the present disclosure is not limited to this.

In step S150, the additional magnetic fields at the positions of the magnetometers 1 are measured by the magnetometers 1 and the measured values of magnetic field $M_B$ of the additional magnetic fields are obtained. And in step S160, during the working process of the magnetometers 1, the additional magnetic fields at the positions of the magnetometers 1 are measured by the magnetometers 1 and the measured working values of magnetic field $M_C$ of the additional magnetic fields are obtained.

Since the calibration gain values K have been obtained in step S140, the actual values of magnetic field $M_1$ of the additional magnetic fields at the positions of the magnetometers 1 can be calculated based on the calibration gain values K and the measured values $M_B$, that is, $M_1 = K \times M_B$. During the working process of the magnetometers 1, since the positions of the magnetic field generating devices 34 are fixed relative to the magnetometers 1, and the magnetic field excitation signals (e.g., excitation current) of the magnetic field generating devices 34 can be set in step S150 to remain unchanged or change with known parameters, the actual values of magnetic field $M_1$ of the additional magnetic fields can remain unchanged or change with known parameters.

Under the condition that the actual values of magnetic field $M_1$ of the additional magnetic fields remain unchanged, that is, $M1 = K' \times M_C$, the detection gain values K' of the magnetometers 1 can be calculated based on the measured values of magnetic field $M_B$ and the measured working values of magnetic field $M_C$. The calculation formula of the detection gain values K' is as follows:

$$K' = K \times M_B / M_C$$

Based on the above principle, whether the detection gain values K' change can be monitored in real time by measuring the additional magnetic fields and obtaining the measured working values of magnetic field $M_C$ of the additional magnetic fields. Similarly, under the condition that the additional magnetic fields change with known parameters, the detection gain values K' of the magnetometers 1 can be calculated by a similar method based on the measured values of magnetic field $M_B$, the parameters of the additional magnetic fields and the measured working values of magnetic field $M_C$, which will not be repeated here.

By way of example, it is determined whether the deviation between the calibration gain values K of the magnetometers and the detection gain values K' is greater than a threshold. If the deviation between the calibration gain values K of the magnetometers and the detection gain values K' is greater than the threshold, an inspection operation is performed.

By way of example, during the working process of the magnetometers, the detection gain values K' of the magnetometers 1 are continuously calculated, and whether the deviation between different detection gain values K' are greater than the threshold is determined. If the deviation of the detection gain values K' of the magnetometers are greater than the threshold, an inspection operation is performed.

The inspection operation related to the above exemplary embodiment aims at checking the causes of the deviation, such as an abnormal magnetometer detection, an abnormal change in the additional magnetic fields or interference by the environmental noise, etc. Those skilled in the art can use appropriate inspection operations to eliminate the causes of the deviation, and the present disclosure is not limited on this.

Optionally, the value of the threshold is in the range of 0.1-5%. For example, the value of the threshold is 0.1%, 0.5%, 1%, 2% or 5%.

By way of example, the calibration method may also comprise turning off the magnetic field generating devices 33 fixedly disposed on the magnetometers 1 during the working process of the magnetometers 1. Through the above steps, the crosstalk between the magnetic fields can be prevented, thus improving the magnetic field detection accuracy of the magnetometers 1, or the devices 33 can be used for other purposes.

Figure 10:
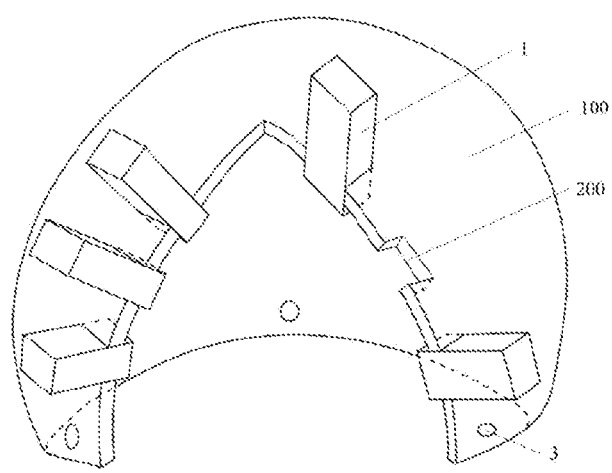
FIG. 10 shows a schematic diagram of a magnetometer holder according to an embodiment of the present invention.

FIG. 10 shows a schematic diagram of a magnetometer holder according to an embodiment of the present invention. An embodiment of the present disclosure further provides a magnetometer holder 100 comprising mounting parts 200 and at least one magnetic field generating device 3. The mounting parts 200 are used for mounting the magnetometers 1. The magnetic field generating devices 3 have the position fixed relative to the magnetometers 1 and are used to generate calibration magnetic fields.

Optionally, the magnetometer holder 100 is rigid or flexible.

Optionally, the magnetometer holder 100 is a helmet.

In this embodiment, the magnetometer holder 100 is rigid, that is, once worn on the head of a subject, the relative positions of different magnetometers 1 on the magnetometer holder 100 will not easily change. The magnetometer holder 100 can be made of nonmagnetic materials, such as photosensitive toughened resin or nano-ceramic materials.

Figure 11:
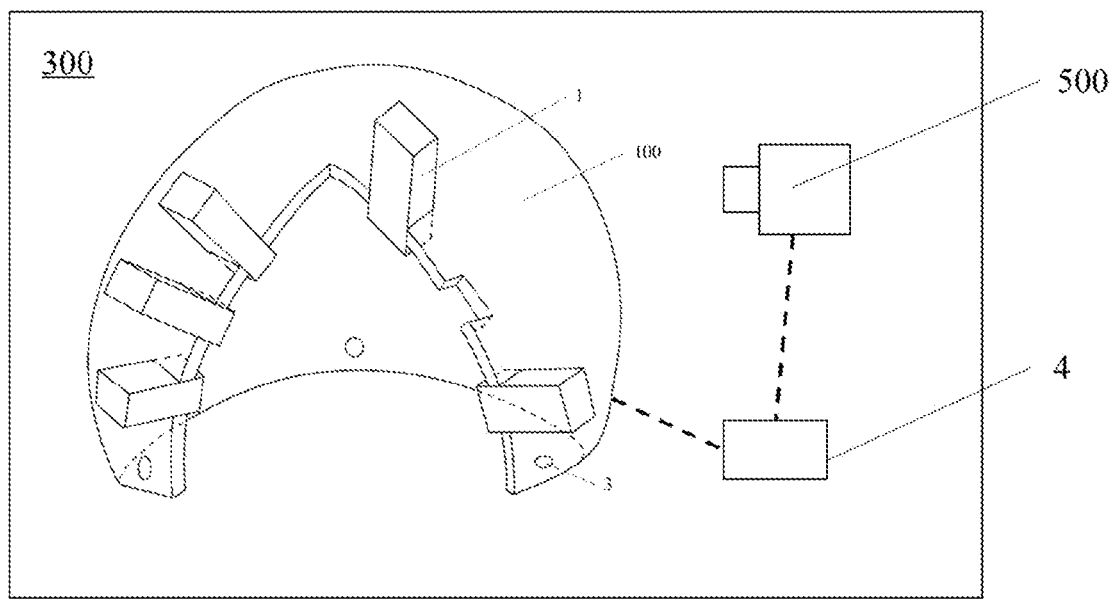
FIG. 11 shows a schematic block diagram of a magnetic detection system according to an embodiment of the present invention.

FIG. 11 shows a schematic block diagram of a magnetic detection system according to an embodiment of the present invention. An embodiment of the present invention also provides a magnetic detection system 300 comprising a magnetometer holder 100, magnetometers 1, a measurement system 500, magnetic field generating devices 3 and a calculation device 4. Referring to the description of the previous embodiments, the magnetometers 1 is mounted on the magnetometer holder 100 and measure the magnitudes of the magnetic field vectors at the positions of the magnetometers 1. The measurement system 500 is configured to measure the spatial positions and orientations of the magnetometers 1 in real time.

The magnetic field generating devices 3 are disposed at predetermined positions and generates calibration magnetic field distributions. The arrangement of the magnetic field generating devices 3 can refer to the description in the previous embodiments, and will not be repeated here.

The calculation device 4 is configured to calculate the calibration actual values of the magnetic field vectors at the positions of the magnetometers 1 based on the spatial positions and orientations of the magnetometers 1 measured by the measuring system 500 and the calibration magnetic field distributions. Furthermore, the calculation device 4 also receives the calibration measured values of the magnetic field vectors measured by the magnetometers 1, and compares the calibration actual values with the calibration measured values to calculate the detection gain values of the magnetometers.

Optionally, the magnetic detection system 300 may further comprise a time domain-frequency domain converter. The converter is configured to convert the time domain signals measured by the magnetometers into frequency domain signals through Fourier transform or other algorithms, and calculate the measured values of target corresponding to the magnetometers through the calibration measured values corresponding to the frequencies of the calibration magnetic fields. The converter extracts signals with predetermined frequencies from the measurement results measured by the magnetometers as the measured values.

The frequencies of the calibration magnetic fields can be selected according to the frequencies of the magnetic field distributions generated by the magnetic field generating devices 3, for example, equal to the frequencies of the magnetic field distributions. Also, signals of other frequencies, which are other than the frequencies of the calibration magnetic fields, are output as the measured values of magnetic field to be measured, said other frequencies can for example be in the range of 1-80 Hz. In a case where the target to be measured is the magnetoencephalography of the human brain, the other frequencies may be 1-150 Hz or 1-200 Hz.

In another embodiment not shown, a magnetic detection system is also provided, which comprises a magnetometer holder, magnetometers, first magnetic field generating devices and a calculation device. Different from the previous embodiments, the first magnetic field generating devices are fixedly disposed on the magnetometers and generate the calibration magnetic fields, while the calculation device is configured to receive the calibration measured values of the calibration magnetic fields obtained by the magnetometers and calculate the calibration gain values of the magnetometers based on the calibration magnetic fields and the calibration measured values.

Optionally, the magnetic detection system may further comprise second magnetic field generating devices. The second magnetic field generating devices have positions fixed relative to the magnetometers and are configured to generate additional magnetic fields. This magnetic detection system is particularly suitable for the calibration method shown in FIG. 9 and its embodiment.

Figure 12:
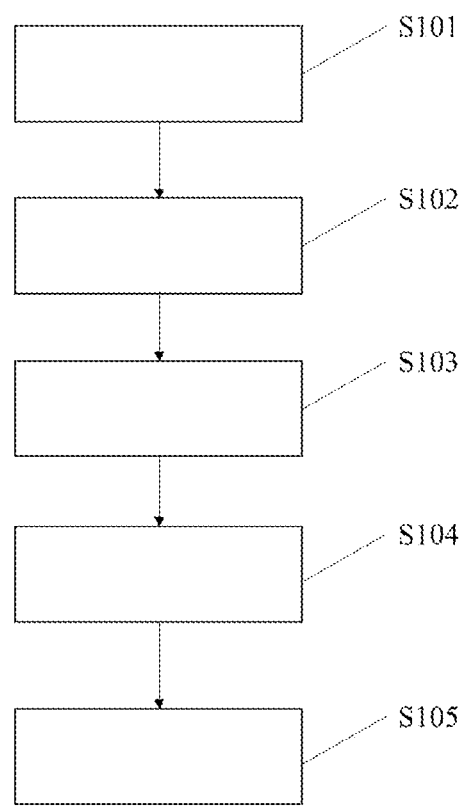
FIG. 12 shows a flowchart of a magnetic detection method according to an embodiment of the present invention.

FIG. 12 shows a flowchart of a magnetic detection method according to an embodiment of the present invention. An embodiment of the invention further provides a magnetic detection method, the method comprising the following steps:

S101. provide magnetometers, the magnetometers being mounted on a magnetometer holder and measuring the magnitudes of magnetic field vectors at positions of the magnetometers as measured values of the magnetometers.

S102. obtaining detection gain values of the magnetometers using the calibration method as described above.

S103. measuring a magnetic field to be measured by the magnetometers to obtain measured values of target.

S104. multiplying the measured values of target of the magnetometers by the detection gain values to obtain actual values of the magnetic field to be measured.

The measured values of target (step S103) and the calibration measured values (step S101) are measured simultaneously, and both of them are used as measurement values of the magnetometers. Further, the measured values of target and the calibration measured values are in different frequency ranges.

Preferably, a step S105 is also included. In the step S105, the measured values by the magnetometers are divided with respect to frequency in order to obtain the calibration measured values and the measured values of target.

Optionally, in the magnetic detection method proposed by the present invention, the magnetic detection can also be carried out continuously and in real time. For example, during the working process of the magnetometers, the positions and orientations of the magnetometers are measured in real time, and the information of the positions and orientations of the magnetometers is input into the calculation device, and the calibration actual values of the magnetic field at the positions of the magnetometers are calculated, and the calibration measured values are compared with the calculated calibration actual values, thereby the detection gain values is continuously calculated. Further, the measurement results of the magnetometers are multiplied by the detection gain values to obtain the actual values of the magnetic field to be measured in real time.

Compared with the traditional SQUID detector array and the calibration method of setting calibration coils at each detector, the calibration system and method provided by the present invention can effectively prevent the crosstalk between detectors, improve the calibration accuracy, and meanwhile can perform calibration in real time, continuously and cooperatively with multiple detectors, so as to obtain accurate multi-detector magnetic field recording results.

The exemplary embodiments of the system and method for spatial positioning of magnetometers proposed by the present invention are described in detail above with reference to preferred embodiments, however, those skilled in the art can understand that many changes and modifications can be made to the above specific embodiments without departing from the concept of the present invention. In addition, the various technical features and structures proposed by various aspects of the present invention can be combined in various ways without exceeding the scope of protection of the present invention, which is determined by the appended claims.

The invention claimed is:

1. A calibration method for magnetometers, comprising:
providing magnetometers mounted on a magnetometer holder, the magnetometers being configured to measure a magnetic field at positions of the magnetometers as measured values of the magnetometers;
providing a plurality of magnetic field generating devices, at least one part of the magnetic field generating devices among the plurality of magnetic field generating devices fixedly disposed on the magnetometers, at least another part of the magnetic field generating devices among the plurality of magnetic field generating devices having their positions fixed relative to the magnetometers, the at least one part of the magnetic field generating devices generating calibration magnetic fields, and the another part of the magnetic field generating devices generating additional magnetic fields which are fixed or changes with known parameters;
measuring, by the magnetometers, calibration measured values of the calibration magnetic fields;
calculating calibration gain values of the magnetometers based on the calibration magnetic fields and the calibration measured values;
measuring, by the magnetometers, measured values of magnetic field of the additional magnetic fields at the positions of the magnetometers;
during a working process of the magnetometers, measuring, by the magnetometers, measured working values of magnetic field of the additional magnetic fields at the positions of the magnetometers, and calculating detection gain values of the magnetometers based on the measured values of magnetic field, parameters of the additional magnetic fields and the measured working values of magnetic field.

2. A magnetic detection system, comprising:
a magnetometer holder;
magnetometers, the magnetometers being mounted on the magnetometer holder and
measuring the magnitudes of magnetic field vectors at positions of the magnetometers as measured values by the magnetometers;
first magnetic field generating devices, the first magnetic field generating devices being fixedly disposed on the magnetometers and generating calibration magnetic fields; and
a calculation device configured to receive calibration measured values of the calibration magnetic fields obtained by the magnetometers and calculate detection gain values of the magnetometers based on the calibration magnetic fields and the calibration measured values.

3. The calibration method according to claim 1, further comprising:
during the working process of the magnetometers, turning off the at least one part of the magnetic field generating devices fixedly disposed on the magnetometers.

4. The calibration method according to claim 3, further comprising:
during the working process of the magnetometers, continuously calculating the detection gain values of the magnetometers, and determining whether deviations of the detection gain values are greater than a threshold, and if a deviation of a detection gain value of a magnetometer is greater than the threshold, performing an inspection operation.

5. The calibration method according to claim 1, wherein the at least another part of the magnetic field generating devices among the plurality of magnetic field generating devices are disposed on the magnetometer holder or the space to be measured.

6. The magnetic detection system according to claim 2, further comprising:
second magnetic field generating devices, the second magnetic field generating devices having positions fixed relative to the magnetometers and being configured to generate additional magnetic fields.

7. The magnetic detection system according to claim 2, wherein the magnetometer holder is a helmet, and the helmet is rigid or flexible.

8. The magnetic detection system according to claim 2, further comprising: a time domain-frequency domain converter, the converter extracting signals of predetermined frequencies from measurement results obtained by the magnetometers as the measured values.

9. The magnetic detection system according to claim 2, wherein the magnetometers are further configured to detect a magnetic field of a target to be detected to obtain measured values of target, and the calculation device is configured to apply the detection gain values to the measured values of target to obtain actual values of the magnetic field to be detected.

10. The calibration method according to claim 3, further comprising:
determining whether deviations between the calibration gain values and the detection gain values of the magnetometers are greater than a threshold, and if a deviation between a calibration gain value and a detection gain value of a magnetometer is greater than the threshold, performing an inspection operation.

11. The magnetic detection system according to claim 9, wherein frequencies of the calibration measured values are different from frequencies of the measured values of target.

12. The calibration method according to claim 10, wherein the value of the threshold is the range of 0.1-5%.

\* \* \* \* \*